US008318813B2

(12) United States Patent  
Sanfilippo

(10) Patent No.: US 8,318,813 B2
(45) Date of Patent: Nov. 27, 2012

(54) METHOD OF TREATING BINGE EATING DISORDER

(75) Inventor: Louis Sanfilippo, New Haven, CT (US)

(73) Assignee: LCS Group, LLC, New Haven, CT (US)

( * ) Notice: Subject to any disclaimer, the term of this patent is extended or adjusted under 35 U.S.C. 154(b) by 0 days.

(21) Appl. No.: 12/666,460

(22) PCT Filed: Jan. 24, 2008

(86) PCT No.: PCT/US2008/001002
§ 371 (c)(1),
(2), (4) Date: Oct. 6, 2010

(87) PCT Pub. No.: WO2009/035473
PCT Pub. Date: Mar. 19, 2009

(65) Prior Publication Data
US 2011/0021564 A1 Jan. 27, 2011

Related U.S. Application Data

(60) Provisional application No. 60/972,046, filed on Sep. 13, 2007.

(51) Int. Cl.
| A61K 31/137 | (2006.01) |
| A61K 45/06 | (2006.01) |
| A61P 25/26 | (2006.01) |
| A61P 25/30 | (2006.01) |
| A61K 31/4458 | (2006.01) |
| A61K 31/16 | (2006.01) |
| A61K 31/35 | (2006.01) |
| A61K 31/423 | (2006.01) |
| A61P 3/04 | (2006.01) |

(52) U.S. Cl. .......................... 514/654; 514/626; 514/630
(58) Field of Classification Search .................. None
See application file for complete search history.

(56) References Cited

U.S. PATENT DOCUMENTS

| 6,317,700 | B1 | 11/2001 | Bagne | |
| 6,323,236 | B2 | 11/2001 | McElroy | |
| 7,678,770 | B2* | 3/2010 | Mickle et al. | 514/17.5 |
| 2005/0038121 | A1* | 2/2005 | Mickle et al. | 514/563 |
| 2008/0249082 | A1 | 10/2008 | Hollander | |

FOREIGN PATENT DOCUMENTS

| WO | 2006121552 A2 | 11/2006 |
| WO | 2007093624 A2 | 8/2007 |

OTHER PUBLICATIONS

Drimmer, E.J., "Stimulant Treatment of Bulimia Nervosa," Nutrition, 19:76-77, (2003).*
Yeomans and Gray, Psychology & Behavior, 62:15-21 (1997).*
Krishnan et al., Biol. Psychiatry, 59:1S-264S, p. 2275 (May 2006).*
Bnge eating disorder. The American Heritage Medical Dictionary (2007).*
Dukarm, Journal of Women's Health, 14(5): 345-350 (2005).*
Sokol et al., International Journal of Eating Disorders, 25: 233-237 (2007).*
Shapira et al., Journal of Clinical Psychiatry, 61: 368-372 (2000).*
McElroy et al., American Journal of Psychiatry, 160: 255-261 (2003).*
Leddy et al., Obesity Research, 12: 224-232 (2004).*
Golay et al., Obesity Research, 13: 1701-1708 (2005).*
Carter et al., International Journal of Eating Disorders, 34 Suppl:S74-88 (2003).*
RITALIN Package Insert (accessed at http://dailymed.nlm.nih.gov/dailymed/drugInfo.cfm?id=34566, Apr. 6, 2012.*
Mattos et al., Rev Bras Psiquiatr. 26(248-250 (2004).*
"Binge-eating disorder", Mayo Clinic, accessed at http://www.mayoclinic.com/health/binge-eating-disorder/DS00608 (2012).*
Hudson et al., Biological Psychiatry, 61(3): 348-358 (2007).*
ADDERALL XR Capsules package insert, Shire US Inc. (2007).*
RITALIN package insert, Novartis Pharmaceuticals Corporation (2010).*
Kessler et al., American Journal of Psychiatry, 163 (4): 716-723 (2006).*
Madaan, et al., "Innovations and recent trends in the treatment of ADHD," Expert Review of Neurotherapeutics, 6(9), 1375-1385 (2006).
Patentability Report for International Application No. PCT/US2008/001002 dated Mar. 25, 2010.
Samanin, et al., "Neurochemical Mechanism of Action of Anorectic Drugs," Pharmacology & Toxicology, 73, 63-68 (1993).
Biederman, et al., "Efficacy and Tolerability of Lisdexamfetamine Dimesylate (NRP-104) in Children with Attention-Deficit/Hyperactivity Disorder: A Phase III, Multicenter, Randomized, Double-Blind, Forced-Dose, Parallel-Group Study," Clinical Therapeutics (2007) 29(3): 450-463.
Blick, et al., "Lisdexamfetamine," Pediatric Drugs, (2007) 9(2): 129-135.
"DSM-IV-TR," Diagnostic and Statistical Manual of Mental Disorders, Fourth Revision 583-595 & 785-787, (2000).
Elia, et al., "Methylphenidate and Dextroamphetamine Treatments of Hyperactivity: Are there True Nonresponders?" Psychiatric Research (1991) (36): 141-155.
Elia, et al., "Treatment of Attention Deficit Hyperactivity Disorder," New England Journal of Medicine, (1999) 340(10): 780-788.

(Continued)

Primary Examiner — Daniel Sullivan
Assistant Examiner — Lisbeth C Robinson
(74) Attorney, Agent, or Firm — Cantor Colburn LLP

(57) ABSTRACT

The invention provides methods of treating binge eating disorders, obesity resulting from binge eating behavior, and depression. The invention includes methods of treating certain co-morbidities in ADHD and ADD patients; for example the invention includes methods of treating generalized anxiety disorder, obsessional and ruminative thought disorders, and obsessive/compulsive behavior in ADHD and ADD patients. The invention also includes combination methods of treatment in which an amphetamine prodrug, methylphenidate prodrug, or methylphenidate analog is administered with one or more other active agents. Packaged pharmaceutical compositions containing an amphetamine or methylphenidate prodrug, instructions for using the prodrug to treat certain disorders, and optionally one or more other active agents are provided by the invention.

13 Claims, No Drawings

OTHER PUBLICATIONS

Fairburn, et al., "The Natural Course of Bulimia Nervosa and Binge Eating Disorder in Young Women," Arch. Gen. Psychiatry, (2000) 57: 659-665.

Goldstein, et al., "Long Term Fluoxetine Treatment of Bulimia Nervosa," British Journal of Psychiatry, (1995) 166: 660-666.

Grilo, et al., "Efficacy of Cognitive Behavioral Therapy and Fluoxetine for the Treatment of Binge Eating Disorder: A Randomized, Double Blind Placebo-Controlled Comparison," Biological Psychiatry, (2005) 57: 301-309.

Modi, et al., "Single- and Multiple-Dose Pharmacokinetics of an Oral Once-a-Day Osmotic Controlled-Release OROS (methylphenidate HCl) Formulation," J. Clin Pharmacol 40: 379-388 (2000).

Vyvanse Package Insert, Feb. 2007.

Wilfley, et al., "Classification of Eating Disorders: Toward DSM-V," Int. J. Eat. Disord. (2007) 40: S123-S129.

Bello, et al., "Acute methylphenidate treatments reduce sucrose intake in restricted-fed bingeing rats," Brain Research Bulletin 70: 422-429 (2006).

Cortese, et al., "Attention-Deficit/Hyperactivity Disorder (ADHD) and Binge Eating," Nutrition Reviews 65(9): 404-411 (2007).

Drimmer, Eric J. MD, "Stimulant Treatment of Bulimia Nervosa With and Without Attention-Deficit Disorder: Three Case Reports," Nutrition 19: 76-77 (2003).

Dukarm, "Bulimia Nervosa and Attention Deficit Hyperactivity Disorder: A Possible Role for Stimulant Medication," Journal of Women's Health 14: 345-350 (2005).

Ong, et al., "Suppression of bulimic symptoms with methylamphetamine," The British Journal of Psychiatry 143: 288-293 (1983).

Schweickert, et al., "Efficacy of Methylphenidate in Bulimia Nervosa Comorbid with Attention-Deficit Hyperactivity Disorder: A Case Report," Int J Eat Disord 21: 299-301 (1997).

Search Report for International Application No. PCT/US2008/001002 dated Oct. 16, 2009.

Sokol, et al., Methylphenidate Treatment for Bulimia Nervosa Associated with a Cluster B Personality Disorder, Int J East Disord 25: 233-237 (1999).

Written Opinion for International Application No. PCT/US2008/001002 dated Oct. 16, 2009.

* cited by examiner

METHOD OF TREATING BINGE EATING DISORDER

This application claims the benefit of U.S. Provisional Patent Application Ser. No. 60/972,046 filed Sep. 13, 2007, and to PCT/US08/001002, filed Jan. 24, 2008, which are incorporated by reference herein in their entirety.

FIELD OF INVENTION

The inventor has discovered that amphetamine prodrugs and methylphenidate prodrugs are useful for treating a number of central nervous system disorders. Methods of treating binge eating disorders, obesity resulting from binge eating behavior, and depression are included herein. The invention includes methods of treating certain co-morbidities in ADHD (Attention-Deficit Hyperactivity Disorder) and ADD patients; for example the invention includes methods of treating generalized anxiety disorder, obsessional and ruminative thought disorders, and obsessive/compulsive behavior in ADHD and ADD patients. Methods of treatment include methods in which the amphetamine prodrug, methylphenidate prodrug, or methylphenidate analog is the only active agent. The invention also includes combination methods of treatment in which an amphetamine prodrug, methylphenidate prodrug, or methylphenidate analog is administered with one or more other active agents. Methods of use described herein include informing a user that an amphetamine prodrug, methylphenidate prodrug, or methylphenidate analog may be used to treat any of the disorders listed above. The invention includes pharmaceutical compositions comprising an amphetamine prodrug, methylphenidate prodrug, or methylphenidate analog together with one or more other active agents in a single dosage form. Packaged pharmaceutical compositions containing an amphetamine prodrug, methylphenidate prodrug, or methylphenidate analog with instructions for using the composition to treat one of the disorders listed above are also provided.

BACKGROUND

Binge Eating Disorder and Obesity Resulting from Binge Eating Disorder

Binge Eating Disorder is a form of Eating Disorder Not Otherwise Specified according the Diagnostic and Statistical Manual of Mental Disorders (DSM-IV-TR). As defined by the DSM-IV-TR, it is characterized by recurrent binge eating episodes.

Commonly described symptoms of binge eating disorder include frequent dieting and weight loss, hoarding of food, hiding empty food containers, eating late at night, attribution of one's successes and failures to weight, avoiding social situations where food may be present, and feeling depressed or anxious. Binge eating also may cause rapid and unhealthy weight gain (or loss), weight fluctuations, and chronic erratic eating behavior. Binge eating disorder and symptoms associated with binge eating disorder may result in obesity though obesity is not necessarily a result of binge eating disorder. Further, patients with binge eating disorder are often not obese and may even have a below normal weight.

The biological basis of binge eating disorder is poorly understood. Binge eating disorder is difficult to treat and carries significant medical and psychiatric risks. Pharmacologic interventions have been of limited success and sometimes cause a worsening of binge eating symptoms. A number of psychotropic medications, including but not limited to antidepressants, antipsychotics, antimanic agents, and mood modulating medications are known to cause binge eating, dysregulation of appetite, and weight gain. Binge eating behaviors and weight gain may be a direct effect of such medication(s). Psychotropic medications may also exacerbate an underlying binge eating disorder in some patients.

Medical complications associated with binge eating disorder include high blood pressure, high cholesterol and triglycerides, kidney disease (and failure), gallbladder disease, arthritis, bone deterioration, stroke, upper respiratory infections, skin disorders, menstrual irregularities, ovarian abnormalities, and pregnancy complications. Psychiatric problems associated with, or exacerbated by, binge eating disorder include depressive disorders, mood disorders, anxiety disorders, ADHD and ADD, personality disorders, other eating disorders, suicidal thoughts, and substance abuse disorders.

Individuals with binge eating disorder may respond to treatment with antidepressants, though such medications may contribute to a worsening of binge eating symptoms, along with weight gain, either at the outset of treatment or over time.
Depression Depression is often difficult to treat, as some patients fail to respond to an initial pharmacologic intervention and a decision must be made to switch agents, augment with another medication(s), or combine multiple pharmacologic agents. Combining medications, while often helpful, can sometimes be problematic with added side effect burdens. Side effects of certain psychotropic medication sometimes used to offer adjunct treatment to patients already taking antidepressants may include weight gain and obesity.

Individuals treated for major depressive disorders may show a positive response or full remission of symptoms to medication treatment, though recent clinical evidence suggests remission rates following an adequate course of monotherapy treatment may as low as 30-40%. Further, clinical studies suggest an unusually large percentage of depressed individuals treated with antidepressant medication, greater than 30-40% in various clinical studies, show only a partial response (for example, full remission is not achieved but there is some measure of improvement in depressive symptoms). Some patients may be 'refractory' or 'resistant' to treatment and fail to respond to one, or in some cases, multiple monotherapy and combination antidepressant medication treatments.

Major depressive disorders similarly may lead to deteriorating physical health and may increase the risk of morbidity and mortality in patients with concurrent medical conditions.

Similarly, depressive disorders are often associated with, or may exacerbate, other mood disorders, anxiety disorders, attention deficit hyperactivity disorder (ADHD or ADD), psychotic disorders, personality disorders, eating disorders, cognition and cognitive disorders, substance abuse disorders, and suicidal ideation.

There exists an unmet and important clinical need for treatments for binge eating disorders, obesity resulting from binge eating behavior, and depression that is only partially responsive to medication and intractable (e.g. 'treatment-resistant') depression. The present invention fulfills this need and provides additional advantages described herein.

SUMMARY OF THE INVENTION

The inventor has discovered that amphetamine prodrugs, including lisdexamfetamine dimesylate, methylphenidate prodrugs, and certain methylphenidate analogs, are useful for treating binge eating disorders, obesity resulting from binge eating behavior, and depression. Furthermore amphetamine prodrugs, methylphenidate prodrugs, and certain methylphenidate analogs have been found useful for treating certain co-morbidities in ADHD and ADD patients. The invention includes methods of treating generalized anxiety disorder, obsessional and ruminative thought disorders, and obsessive/compulsive behavior in patients, particularly in ADHD/ADD patients. Methods of using amphetamine prodrugs, methylphenidate prodrugs, or methylphenidate analogs, as a monotherapy for treating these conditions and disorders or in combination with one or more other active agents are provided herein.

The invention includes a method of treating binge eating disorder or obesity resulting from binge eating behavior, comprising diagnosing a patient as having a binge eating disorder or obesity resulting from binge eating behavior and providing an effective amount of amphetamine prodrug, methylphenidate prodrug, or methylphenidate analog to the patient.

The invention also includes a method of treating depression comprising diagnosing a patient as having depression and providing an effective amount of amphetamine prodrug, methylphenidate prodrug, methylphenidate analog to the patient.

The invention further provides a method of treating generalized anxiety disorder, obsessional and ruminative thought disorders, or obsessive/compulsive behavior in a patient having ADHD or ADD or other patient. In an ADHD or ADD patient this method comprises diagnosing a patient having ADHD or ADD and as also having at least one of generalized anxiety disorder, obsessional and ruminative thought disorders, or obsessive/compulsive behavior, and providing an effective amount of amphetamine prodrug, methylphenidate prodrug, or methylphenidate analog to the patient.

In each of these methods the amphetamine prodrug, methylphenidate prodrug, or methylphenidate analog may be provided as the only active agent, i.e. as a monotherapy, or may be provided together with one or more other active agents, i.e. as a combination, adjunct, or augmentation therapy.

In a separate embodiment, the invention includes a method of using an amphetamine prodrug, methylphenidate prodrug, or methylphenidate analog comprising informing a user that the amphetamine prodrug, methylphenidate prodrug, methylphenidate analog may be used to treat binge eating disorder or obesity resulting from binge eating behavior. The invention also includes a method of using an amphetamine prodrug, methylphenidate prodrug, or methylphenidate analog comprising informing a user that the amphetamine prodrug, methylphenidate prodrug, or methylphenidate analog may be used to treat depression. The invention further includes a method of using an amphetamine prodrug, methylphenidate prodrug, or methylphenidate analog comprising informing a user that the amphetamine prodrug, methylphenidate prodrug, methylphenidate analog may be used to treat certain co-morbidities in ADHD and ADD patients, or may be used to treat certain CNS disorders in patients not diagnosed with ADHD or ADD, including generalized anxiety disorder, obsessional and ruminative thought disorders, and obsessive/compulsive behavior. The invention includes (i) lisdexamfetamine dimesylate and (ii) one or more other active agent(s) combined in a single dosage form.

The invention includes articles of manufacture comprising an amphetamine prodrug, methylphenidate prodrug, or methylphenidate analog in a container and printed labeling. The printed labeling states that the amphetamine prodrug, methylphenidate prodrug, or methylphenidate analog is useful for treating a binge eating disorder, obesity resulting from binge eating behavior, or depression. In other embodiments the printed labeling states that the amphetamine prodrug, methylphenidate prodrug, methylphenidate analog is useful for treating generalized anxiety disorder, obsessional and ruminative thought disorders, and obsessive/compulsive behavior in a patient, particularly in a patient having ADHD or ADD.

DETAILED DESCRIPTION

Terminology

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced item.

An "active agent" means any compound, element, or mixture that when administered to a patient alone or in combination with another agent confers, directly or indirectly, a physiological effect on the patient. When the active agent is a compound, salts, solvates (including hydrates) of the free compound or salt, crystalline and non-crystalline forms, as well as various polymorphs of the compound are included. Compounds may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers in pure form and mixtures thereof are encompassed. In addition, compounds with carbon-carbon double bonds may occur in Z- and E-forms, with all isomeric forms of the compounds being included in the present invention. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. A "dosage form" means any unit of administration of an active agent.

"Binge eating disorder" is a form of Eating Disorder Not Otherwise Specified. As defined by the DSM-IV-TR, it is characterized by recurrent binge eating episodes. Such episodes include eating larger amounts of food than normal during a short period of time (for instance, within a two hour period) and a lack of control over eating during the binge episode (for instance, one cannot stop eating). According to the DSM-IV-TR, binge eating disorders are associated with three or more of the following symptoms: eating until uncomfortably full; eating large amounts of food when not physically hungry; eating much more rapidly than normal; eating alone on account of embarrassment over how much one is eating; and feeling disgusted, depressed or guilty after overeating. Additionally, individuals with binge eating disorder feel distress about their binging behavior. The DSM-IV-TR also characterizes binge eating to occur, on average, at least 2 days a week for six months, while not being associated with the regular use of inappropriate compensatory behaviors such as purging or excessive exercise and not occurring exclusively during the course of bulimia nervosa or anorexia nervosa. As used herein "depression" includes major depressive disorder, dysthymic disorder, depressive disorder not otherwise specified (for instance, premenstrual dysphoric disorder), and depressive episodes that may be present in another disorder (e.g. as in other mood disorders such as bipolar disorder or a mood disorder due to a general medical condition).

Depressive disorders represent one of four classes of mood disorders listed in the DSM-IV-TR; the other major forms of mood disorders include bipolar disorders, mood disorders due to a general medical condition, and substance-induced mood disorders, all of which may demonstrate symptoms of depression or low mood. Major depressive episodes may be present in a depressive disorder, which according to the DSM-IV-TR include major depressive disorder, dysthymic disorder, and depressive disorder not otherwise specified (for instance, premenstrual dysphoric disorder).

Depressive symptoms or features such as low mood, diminished interest in activities, psychomotor slowing or agitation, changes in appetite, poor concentration or indecisiveness, excessive guilt or feelings of worthlessness, and suicidal ideations may occur in the context of depressive disorders, bipolar disorders, mood disorders due to a general medical condition, substance-induced mood disorders, other unspecified mood disorders, and also may be present in association with a range of other psychiatric disorders, including but not limited to psychotic disorders, cognitive disorders, eating disorders, anxiety disorders and personality disorders. The longitudinal course of the disorder, the history and type of symptoms, and etiologic factors help distinguish the various forms of mood disorders from each other.

A "major depressive episode, according to the DSM-IV-TR, involves five or more of the following symptoms in the same 2 week period, signifying a change from previous functioning, of which one symptom is either 1) depressed mood or 2) a loss of interest or pleasure. The other symptoms include weight loss or weight gain, insomnia or hypersomnia, psychomotor retardation or agitation, fatigue or lethargy, feelings of worthlessness or excessive guilt, poor concentration, or recurrent thoughts of death or suicide. Such symptoms cause significant distress or impairment and are not due to a general medical or substance abuse condition.

"Depression symptoms rating scale" refers to any one of a number of standardized questionnaires, clinical instruments, or symptom inventories utilized to measure symptoms and symptom severity in depression. Such rating scales are often used in clinical studies to define treatment outcomes, based on changes from the study's entry point(s) to endpoint(s). Such depression symptoms rating scales include, but are not limited to, The Quick Inventory of Depressive-Symptomatology Self-Report (QIDS-SR$_{16}$), the 17-Item Hamilton Rating Scale of Depression (HRSD$_{17}$), the 30-Item Inventory of Depressive Symptomatology (IDS-C$_{30}$), or The Montgomery-Asperg Depression Rating Scale (MADRS). Such ratings scales may involve patient self-report or be clinician rated. A 50% or greater reduction in a depression ratings scale score over the course of a clinical trial (starting point to endpoint) is typically considered a favorable response for most depression symptoms rating scales. "Remission" in clinical studies of depression often refers to achieving at, or below, a particular numerical rating score on a depression symptoms rating scale (for instance, less than or equal to 7 on the HRSD$_{17}$; or less than or equal to 5 on the QIDS-SR$_{16}$; or less than or equal to 10 on the MADRS).

Binge eating behavior may be assessed by different methods though is commonly determined by the frequency of binge eating episodes occurring over a specific period of time (i.e., the number of binges per week; or the mean number of binges over two week periods). Another form of assessment may quantify the number of "binge-days", that is, the number of days in which the patient has binged in any form (i.e., whether once or multiple times) and determining the frequency of binge-days over a specific time frame.

"Generalized Anxiety Disorder" as defined by the DSM_IV-TR, and as the term is used herein, is a disorder meeting the following criteria: A. At least 6 months of "excessive anxiety and worry" about a variety of events and situations. Generally, "excessive" can be interpreted as more than would be expected for a particular situation or event. Most people become anxious over certain things, but the intensity of the anxiety typically manifests in the following manner:

A. There is significant difficulty in controlling the anxiety and worry.

B. The presence for most days over the previous six months of 3 or more (only 1 for children) of the following symptoms: 1. Feeling wound-up, tense, or restless, 2. Easily becoming fatigued or worn-out, 3. Concentration problems, 4. Irritability, 5. Significant tension in muscles, and 6. Difficulty with sleep.

C. The symptoms are not part of another mental disorder.

D. The symptoms cause "clinically significant distress" or problems functioning in daily life. "Clinically significant" is the part that relies on the perspective of the treatment provider. Some people can have many of the aforementioned symptoms and cope with them well enough to maintain a high level of functioning.

E. The condition is not due to a substance or medical issue. The severity of Generalized Anxiety Disorder may be assessed using a commonly accepted test for assessing the anxiety severity, such as the Hamilton Anxiety Rating Scale (HAM-A) or the Generalized Anxiety Disorder Severity Scale (GADSS).

"Obsessive behavior" may arise in many different clinical forms, including recurrent thoughts, impulses or images; perseverative thinking patterns; or highly ruminative mental behavior. Such symptoms often, but not necessarily, occur in the context of obsessive-compulsive disorder. "Compulsive behavior," sometimes referred to as 'compulsions', may similarly take a myriad of clinical forms, from more conventional obsessive-compulsive disorder symptoms (i.e., "checking", "ordering" or "hoarding" behaviors) to such symptoms as compulsive gambling and substance abuse, sexual and internet compulsions, and compulsive exercising or lying. The Yale-Brown Obsessive Compulsive Scale (Y-BOCS) is often used to assess symptom severity for patients that have both obsessions and compulsions, with scores reflecting symptoms severity (for instance, 0-7 as 'sub-clinical' through 32-40 as 'severe').

"Obesity" is defined as a BMI (Body Mass Index)>30 (kg/m$^2$).

"Efficacy" means the ability of an active agent administered to a patient to produce a therapeutic benefit in the patient.

The terms "amphetamine prodrug" and "methylphenidate prodrug" refer to any product that contains either an amphetamine (CAS Reg. No. 300-62-9) or methylphenidate (CAS Reg. No. 113-45-1) compound conjugated to a chemical moiety such that the conjugated amphetamine or methylphenidate must undergo a conversion in a patient's body to become the active amphetamine or methylphenidate form. "Amphetamine" includes dextro and levo amphetamine forms and all pharmaceutically acceptable amphetamine salts. Conversion typically involves metabolism. "Methylphenidate" also includes all methylphenidate optical isomers and all pharmaceutically acceptably methylphenidate salts. For example "methylphenidate" includes pure dexmethylphenidate (α-phenyl-2-piperidineacetatehydrochloride, (R,R')-(+)-) and racemic mixtures of d- and l-methylphenidate forms.

Lisdexamfetamine dimesylate, CAS Reg. No. 608137-32-3, (2S)-2,6-diamino-N-[(1S)-1-methyl-2-phenylethyl]hexanamide dimethanesulfonate, is an amphetamine prodrug in which L-lysine is covalently bound to d-amphetamine. Lisdexamfetamine dimesylate is sold under the trade name VYVANSE (Shire). It has the chemical formula:

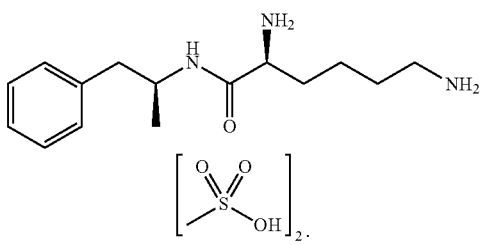

"Lisdexamfetamine" is typically administered as a dimesylate salt but includes all pharmaceutically acceptable salts of lisdexamfetamine free base. The term "lisdexamfetamine" also encompasses all polymorphs and hydrates of this drug.

"Informing" in any of the above embodiments of the invention may occur by reference to, or providing, information material. Informing can also occur by presentation at a seminar, conference, or other educational presentation; or by providing an active agent with informational material to a user; or in a conversation between a pharmaceutical sales representative and a medical care worker or between a medical care worker and a patient.

"Informational material" means any media providing information. Media includes printed, audio, visual, or electronic media. Examples of information material are flyer, an advertisement, a package insert for a pharmaceutical product, printed labeling, an internet web site, an internet web page, an internet pop-up window, or information recorded on a compact disk, DVD, an audio recording, or any other recording or electronic medium.

A "medical care worker" means any worker in the health care field who may need information regarding an active agent, including information on safety, efficacy, dosing, administration, or pharmacokinetics. Examples of medical workers include physicians, pharmacists, physician's assistants, nurses, caretakers, emergency medical workers, and veterinarians.

A "patient" means any human or non-human animal in need of medical treatment. Medical treatment can include treatment of an existing condition, such as a disease or disorder, prophylactic or preventative treatment, or diagnostic treatment. In some embodiments the patient is a human patient.

As used herein "a pharmaceutical supplier" means any person (other than a medical care worker), business, charitable organization, governmental organization, or other entity involved in the transfer of active agent between entities, for profit or not. Examples of pharmaceutical suppliers include pharmaceutical distributors, pharmacies (online or physical), foreign businesses or individuals importing active agent into the United States, the hospitals, HMOs and the Veterans Administration.

"Pharmaceutically acceptable salts" includes derivatives of the disclosed compounds, wherein the parent compound is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts.

Pharmaceutically acceptable organic salts include salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like, and combinations comprising one or more of the foregoing salts.

"Providing" includes giving, selling, distributing, transferring (for profit or not), manufacturing, compounding or dispensing.

A "product" or "pharmaceutical product" is a dosage form of an active agent plus published material and optionally packing.

"Safety" means the incidence of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

The term "therapeutically effective amount" or "effective amount" means an amount effective, when administered to a human or non-human patient, to provide any therapeutic benefit. A therapeutic benefit may be an amelioration of symptoms, e.g., an amount effective to decrease the symptoms of binge-eating disorder or a major depressive disorder. In certain circumstances a patient may not present symptoms of a condition for which the patient is being treated. Thus a therapeutically effective amount of a compound is also an amount sufficient to provide a significant positive effect on any indicia of a disease, disorder or condition e.g. an amount sufficient to significantly reduce the frequency and severity of binge eating behavior or depressive symptoms. A significant effect on an indicia of a disorder or condition includes a statistically significant in a standard parametric test of statistical significance such as Student's T-test, where $p<0.05$; though the effect need not be significant in some embodiments.

A "user" is a patient, a medical care worker, or a pharmaceutical supplier.

Amphetamine and Methylphenidate Prodrugs
Amphetamine has the chemical formula

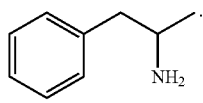

Amphetamine prodrugs, and methods of preparing amphetamine prodrugs have been described previously. U.S. Pat. No. 7,105,486, which describes the preparation of lisdexamfetamine, is hereby incorporated by reference at cols. 20 to 22 for its teachings regarding the synthesis of amino acid amphetamine prodrugs. In addition to amino acid prodrugs it is possible to prepare a number of other amphetamine prodrugs by reacting the amphetamine amino group with a chemically labile moiety. It is within the ability of those of ordinary skill in the art of chemical synthesis to prepare carboxamide amphetamine prodrugs by reacting amphetamine with an aliphatic aldehyde and to prepare carbamate amphetamine prodrugs by reacting amphetamine with an aliphatic organic acid.

Methylphenidate has the chemical formula

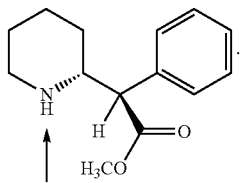

The arrow indicates a chemically accessible site at which labile groups may be added to create methylphenidate prodrugs. Amino acid methylphenidate prodrugs may be prepared via the general methods described in U.S. Pat. No. 7,105,486 for the preparation of amphetamine amino acid prodrugs. Amino acid methylphenidate prodrugs may comprise methylphenidate covalently bound to a single amino acid at the piperidine nitrogen or bound to a di- or tri-peptide at this position. It is also a matter of routine organic synthesis to prepare carboxamide and carbamate methylphenidate prodrugs by reacting methylphenidate with an aliphatic aldehyde or aliphatic organic acid.

Methylphenidate contains a secondary amine group and amphetamine contains an amino group both of which may be reacted to form prodrugs having a chemical moiety covalently attached to the amine or amino group of the parent drug compound. Prodrugs of amine-containing compounds have been disclosed in U.S. Patent Application No. 2007/0123468, which is hereby incorporated by reference at paragraphs [0078]-[0137] for its teaching regarding general classes of amine prodrugs, at paragraph [0140] for its teaching regarding amphetamine and methylphenidate prodrugs, at paragraphs [0176]-[0181] for its teachings of methylphenidate prodrug structures, and at paragraphs [0184]-[0189] for its teaching regarding prodrugs synthesis.

Methylphenidate Analogs

Methylphenidate analogs are compounds have a structure highly similar to methylphenidate, and like methylphenidate bind to the brain dopamine transporter and affect the reuptake of dopamine in the brain, but which have an extended duration of action relative to methylphenidate. Methylphenidate analogs include compounds having the general formula

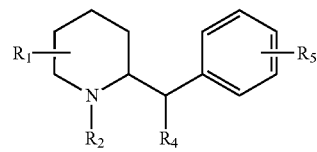

where at least one of $R_2$ and $R_4$ is a non-hydrogen substituent differing from the group that occurs at the corresponding position in methylphenidate and $R_1$ and $R_5$ are independently chosen from hydrogen, halogen, hydroxyl, $C_1$-$C_2$alkyl, and $C_1$-$C_2$alkoxy, and the like. Methylphenidate analogs have been disclosed in U.S. Non-provisional Patent Application No. 2006/0100243, which is hereby incorporated by reference at paragraphs [0007]-[0021] for its teachings regarding the methylphenidate analog structures, at paragraphs [0055]-[0063] for its teachings regarding the methylphenidate analog structure and synthesis, and at paragraphs [0083]-[0085] for its exemplary synthesis of methylphenidate analogs.

Methods of Treatment

The invention provides methods of treating binge eating disorders, obesity resulting from binge eating behavior, and depression. The invention includes methods of treating certain co-morbidities in ADHD and ADD patients; the invention includes methods of treating generalized anxiety disorder, obsessional and ruminative thought disorders, and obsessive/compulsive behavior in patients, particularly in ADHD and ADD patients. The amphetamine prodrug, methylphenidate prodrug, or methylphenidate analog may be the only active agent administered (monotherapy) or may be combined with one or more other active agents (combination, adjunct, or augmentation therapy).

The invention also provides methods of treating depression, weight gain and/or obesity associated with depression, and weight gain and/or obesity due to taking anti-depressant medications.

The invention provides a method of treating chronic fatigue syndrome, fatigue, amotivation, or cognitive deficits associated with fatigue comprising diagnosing a patient as having chronic fatigue syndrome, fatigue, amotivation or cognitive deficits associated with fatigue and providing an effective amount of amphetamine prodrug, methylphenidate prodrug, or methylphenidate analog to the patient.

In a first embodiment the invention includes a method of treating binge eating disorder or obesity resulting from binge eating behavior, comprising diagnosing a patient as having a binge eating disorder or obesity resulting from binge eating behavior and providing an effective amount of amphetamine prodrug, methylphenidate prodrug, or methylphenidate analog to the patient, wherein the amphetamine prodrug, methylphenidate prodrug, or methylphenidate analog is provided as the only active agent or is provided together with one or more additional active agents.

In another embodiment the invention provides a method of treating depression comprising (i) diagnosing a patient as having depression and (ii) providing an effective amount of amphetamine prodrug, methylphenidate prodrug, or methylphenidate analog to the patient, wherein the amphetamine prodrug, methylphenidate prodrug, or methylphenidate analog is provided as the only active agent or is provided together with one or more additional active agents.

Psychosocial intervention may play an important role in treatment of both depression and binge eating disorder. Psychosocial intervention includes cognitive-behavior therapy, dialectical-behavior therapy, interpersonal therapy, psychodynamic therapy and group therapy.

While amphetamine and methylphenidate based stimulant medications have been associated with the side effect of appetite suppression and enhanced mood, their release mechanisms are of short or intermediate duration. As plasma levels of these drugs drop, patients typically experience symptoms associated with low drug levels. Even extended release amphetamine or methylphenidate formulations leave individuals with a 'wear off' effect for a sufficient part of the day, in which the medication loses its effects including appetite suppressant properties. 'Wear off' effects lead to problematic symptoms or side effects, sometimes of a 'rebound' nature, including the urge to have more medication, feeling dysphoric or low, feeling hungry or eating more, binge eating, fatigue, amotivation, and poor concentration.

Lisdexamfetamine dimesylate, given its slower and gradual release, confers certain significant advantages not seen previously with other amphetamine or methylphenidate stimulants. There is minimal 'wear-off' effect, a smoother distribution of drug over time, and no apparent need for dosing beyond once per day as significant effects have been demonstrated for up to 12 hours after administration. The unique clinical profile of lisdexamfetamine dimesylate offers all the benefits of a stimulant treatment for a full day, a much-needed advance required for sustained clinical benefit in depressive and binge eating disorders. Such a profile is particularly significant for depressive disorders, where a low mood is characteristically present through the entire day and often worse later in the day. Problems with concentration or fatigue, associated with depression or which may be associated with other conditions, may receive notably significant benefit as well. Additionally, treatment of binge eating behavior with lisdexamfetamine dimesylate, where symptoms may intensify toward the end of the day or in the evening or may have some relation to feelings of dysphoria as other stimulant medications 'wear off', would achieve surprisingly positive benefit. Lisdexamfetamine dimesylate is thought to confer less 'euphorgenic' properties, which may also mitigate feeling down as the medication "wears off."

Lisdexamfetamine dimesylate, sold under the trade name VYVANSE (Shire), is FDA approved for the treatment of Attention-Deficit Hyperactivity Disorder. Other psychostimulant treatments for Attention-Deficit Hyperactivity Disorder include both amphetamine (e.g. ADDERALL and ADDERALL XR) and methylphenidate (e.g. RITALIN and CONCERTA) preparations. Stimulant drugs, including lisdexamfetamine dimesylate, are believed to act via potentiation of dopamine and norepinephrine neurotransmission in the central nervous system.

Amphetamine prodrugs, including lisdexamfetamine, methylphenidate prodrugs, and certain methylphenidate analogs are unexpectedly effective for treating a number of disorders exacerbated by non-chemically modified immediate release and extended release amphetamine and methylphenidate including binge eating disorder and depression. In certain embodiments a patient is diagnosed as having a binge eating disorder or obesity related to binge eating behavior and an amount of amphetamine prodrug, methylphenidate prodrug, or methylphenidate analog is provided to the patient; wherein the amount is effective to reduce the number of binge eating episodes in a one month time period, to produce a weight loss of 5% or greater of the patient's body mass within a six month treatment period, or significantly reduce the patient's triglyceride levels by 20% or more over a six month treatment period.

Methods of treatment include administering an effective amount of an amphetamine prodrug, methylphenidate prodrug, or methylphenidate analog wherein the effective amount is an amount effective to decrease the number of binge eating episodes per month or decrease the number of days in a month in which the patient experiences a binge eating episode.

In other embodiments the effective amount of amphetamine prodrug, methylphenidate prodrug, or methylphenidate analog is an amount effective to decrease depressive symptoms. Preferably the decrease in depressive symptoms is a 50% or greater reduction of symptoms identified on depression symptom rating scale or is constituted by a depression symptom rate scale score below a particular value that may signify remission of a depressive episode (for instance, less than or equal to 7 on the $HRSD_{17}$).

The invention provides methods of treating weight gain associated with depression or caused by treatment with antidepressant medications.

Treatment approaches for major depressive disorder or other disorders in which depressive symptoms are present typically do not include the management of obesity. Similarly, treatment approaches for obesity typically do not address depressive symptoms. Pharmacologic treatments for mood disorders may actually contribute to weight gain, obesity, or increased abdominal girth, with potentially untoward psychological effects or medical sequelae such as hypertriglyceridemia, metabolic syndrome, or type II diabetes. While the mood disorder or depressive symptoms may be effectively treated with such pharmacologic agents, associated weight gain can carry a number of serious risks. Treatments that address both depression and obesity, as either monotherapy or as adjunct treatment, are much needed clinically and would serve a population with unmet clinical needs. Further, as demonstrated by the putative link of binge eating to such conditions as depression and obesity, pharmacologic interventions that ameliorate binge eating may have particular added value.

The relationship between mood disorders and obesity has been examined in a number of clinical and demographic studies, though the relationship is complicated and poorly understood. Current paradigms that link the two conditions suggest the possibility that shared genetic vulnerabilities, neurobiology (in particular the hypothalamic-pituitary-adrenocortical [HPAC] axis), or social factors may play important roles. Demographic studies suggest obesity, including associated conditions of 'overweight' and 'abdominal obesity,' are common to patients treated for mood disorders and represent a risk factor for depression, in particular for females, children, and individuals with child-onset major depression. It is well established that major depressive disorder commonly will present with 'atypical' features, as recognized in the DSM-IV-TR, with symptoms of weight gain, low energy, and inactivity. Binge eating symptoms may also accompany such forms of depression. Interestingly, obese individuals with binge eating disorder or behavior have been shown to have higher rates of mood disorders. There is research to suggest that women having major depressive disorder may be particularly disposed to weight gain and obesity and, as such, may represent either a distinct subset of depression or of obesity, which may even be linked to polycystic ovarian syndrome. More recent data suggests an even more conclusive link between obesity and atypical features of depression in women with bipolar disorder. In fact, the DSM-IV-TR recognizes that 'atypical' features of depression are 2-3 times more common in women than in men.

The invention further includes methods of using lisdexamfetamine dimesylate, comprising informing a user that the lisdexamfetamine dimesylate may be used to treat binge eating disorders, obesity resulting from binge eating behavior, or depression. The invention includes methods of using lisdexamfetamine dimesylate comprising informing a user that the lisdexamfetamine dimesylate may be used to treat certain co-morbidities in ADHD and ADD patients, including methods of treating generalized anxiety disorder, obsessional and ruminative thought disorders, and obsessive/compulsive behavior in ADHD and ADD patients. The user may be informed of the usefulness of lisdexamfetamine dimesylate, or other amphetamine prodrug, a methylphenidate prodrug, or a methylphenidate analog for the treatment of the above-mentioned disorders and conditions by reference to a package insert associated with the container. The informing may also be by reference to information material; by reference to a package active agent insert, a flyer or an advertisement; by presentation of information at a seminar, conference, or other educational presentation; or by a conversation between a pharmaceutical sales representative and a medical care worker.

Frequency of dosage may vary depending on the compound used and the particular condition or disorder to be treated or prevented. For most disorders a dosage regimen of once per day is preferred. Dosage regimens in which the amphetamine prodrug or methylphenidate prodrug is administered 2 times daily may occasionally be more helpful. In certain embodiments, 2.5 mg to 250 mg lisdexamfetamine dimesylate is administered per day or 15 to 100 mg lisdexamfetamine dimesylate per day, or about 50 mg per day lisdexamfetamine dimesylate is administered. Lisdexamfetamine dimesylate is typically administered once daily in the morning, with preferred dosing in the range of 15-70 mg per day, though in some embodiments daily doses of less than 15 mg, for example from about 2.5 mg to about 15 mg, or from about 2.5 to about 12.5 mg are useful for treating binge eating behaviors or depression.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease in the patient undergoing therapy. Patients may generally be monitored for therapeutic effectiveness using assays suitable for the condition being treated or prevented, which will be familiar to those of ordinary skill in the art.

Combination Methods

The invention provides a method of treating of central nervous system disorders in which an amphetamine prodrug, methylphenidate prodrug, or methylphenidate analog is provided to a patient together with one or more additional active agents. Such methods are referred to as "combination methods" of treatment. Combination methods of treating binge eating disorders, obesity resulting from binge eating behavior, and depression are included herein. The invention includes combination methods of treating certain co-morbidities in ADHD and ADD patients; for example the invention includes combination methods of treating generalized anxiety disorder, obsessional and ruminative thought disorders, and obsessive/compulsive behavior in ADHD and ADD patients.

The additional active agent may be administered separately from the amphetamine prodrug, methylphenidate prodrug, or methylphenidate analog or may be combined with the additional active agent.

The invention also includes combination methods of treatment in which an amphetamine prodrug, methylphenidate prodrug, or methylphenidate analog is administered together with one or more forms of therapy, psychosocial support, or medical management. Such forms of psychosocial intervention include cognitive-behavior therapy, dialectical-behavior therapy, interpersonal therapy, psychodynamic therapy and group therapy.

The invention also includes combination methods of treatment in which the one or more other active agent(s) is an appetite suppressant, a weight loss drug, an anti-obesity agent, an anti-diabetes agent, an antidepressant, an anxiolytic, a selective serotonin reuptake inhibitor, a serotonin 5HT receptor partial agonist or antagonist, a norepinephrine dopamine reuptake inhibitor, a serotonin norepinephrine dopamine reuptake inhibitor, a serotonin 5-HT1a partial agonist, a serotonin 5-HT1b agonist, a serotonin 5-HT2 antagonist, a serotonin 5-HT6 antagonist, a serotonin-2 antagonist reuptake inhibitor, a serotonin-1 agonist reuptake inhibitor, a mixed serotonin antagonist reuptake inhibitor/partial agonist/dopamine agonist, an alpha-2 antagonist/serotonin 5HT2-3 receptor antagonist, a serotonin modulator or stimulator, a mixed serotonin antagonist/melatonin agonist, a mixed serotonin dopamine antagonist, a tricyclic antidepressant, a tetracyclic antidepressant, a bis-aryl-sulphanyl modulator, a beta-3 adrenoreceptor stimulator or agonist, a beta-3 adrenoreceptor antagonist, a nicotinic acetylcholine receptor agonist or antagonist, an enkephalinergic modulator, an aprepitant, a neurokinin (NK) antagonist, a NK1, 2, or 3 antagonist, a neuropeptide (NP)Y antagonist, a NPY1, 2, or 3, or 5 antagonist, a substance P antagonist, a corticotrophin-releasing hormone (CRH or CRF) antagonist, a CRH (or CRF)-1 antagonist, a glucocorticoid receptor agonist or partial agonist, a glucocorticoid receptor antagonist, a glucocorticoid receptor type II antagonist, an anti-convulsant, a GABA modulator, a GABA inverse agonist or partial agonist, a GABA receptor antagonist, a GABA channel antagonist, a GABA reuptake inhibitor, a glutamate modulator, an mGluR receptor modulator, agonist or antagonist, an mGluR2/3 agonist, an mGluR5 antagonist, an estrogen receptor agonist or antagonist, a melatonin receptor agonist or antagonist, a glycine transporter inhibitor, an alpha-1 receptor agonist, an alpha-1 receptor antagonist, an alpha-2 receptor agonist, an alpha-2 receptor antagonist, a vasopressin-1B (V1B) agonist or antagonist, an NMDA receptor modulator (i.e., a partial agonist, agonist, or antagonist), an ampakine modulating agent, an opioid antagonist, an opioid partial agonist, a benzodiazepine, an anti-psychotic, a dopamine receptor agonist or analog, a wakefulness promoting agent, an anti-manic agent, a mood modulating (i.e., stabilizing) agent, a cholinesterase inhibitor, an anti-amyloid agent, an anti-aggregant, a beta-secretase inhibitor, a beta-amyloid antagonist, a monoamine oxidase inhibitor, an anti-migraine agent, a melanocyte inhibiting factor, or a combination of the foregoing.

Weight-loss drugs include, but are not limited to, lipase inhibitors. Non-limiting examples of weight loss drugs include orlistat.

Anti-diabetes drugs include, but are not limited to, hypoglycemic agents. Non-limiting examples include acarbose, chlorpromide, exenatide, gliclazide, glimepiride, glipizide, glyburide, insulin, metformin, miglitol, nateglinide, pioglitazone, pramlintide, repaglinide, rosiglitazone, and tolazamide.

Anti-psychotics include atypical anti-psychotics. Non-limiting examples of anti-psychotics include clozapine, olanzapine, risperidone, aripiprazole, quetiapine, paliperidone, ziprasidone, and amisulpride.

Anti-convulsants include, but are not limited to, anti-epileptics and anti-seizure medications. Non-limiting examples of anti-convulsants include topiramate, lamotrigine, pregabalin, tiagabine, and zonisamide.

Selective serotonin reuptake inhibitors include, but are not limited to, citalopram, escitalopram, femoxetine, fluoxetine, fluvoxamine, paroxetine, sertraline, and zimeldine.

Serotonin partial agonists include, but are not limited to, pindolol, gepirone, and flesinoxan.

Selective serotonin norepinephrine reuptake inhibitors include, but are not limited to, duloxetine, venlafaxine, desvenlafaxine, milnacipran, and clovoxamine.

Norepephrine reuptake inhibitors include, but are not limited to, atomoxetine and reboxetine.

Serotonin-2 antagonist reuptake inhibitors include, but are not limited to, trazodone.

Alpha-2 antagonist/serotonin 5HT2-3 receptor antagonists include, but are not limited to, mirtazapine.

Norepinephrine dopamine reuptake inhibitors include, but are not limited to bupropion.

Tricyclic antidepressants include, but are not limited to, doxepin, amitriptyline, amoxapine, clomipramine, desipramine, doxepin, imipramine, maprotiline, nortriptyline, protriptyline, and trimipramine.

Benzodiazepines include but are not limited to, alprazolam, clonazepam, diazepam, lorazepam, flurazepam, and bentazepam.

Anti-manics include, but are not limited to, carbamazepine, valproic acid and lithium.

Alpha-2 receptor agonists include but are not limited to guanfacine and clonidine.

Wakefulness promoting agents include but are not limited to modafinil and armodafinil.

Neurokinin-1 antagonists include but are not limited to casopitant.

Neurokinin-2 antagonists include but are not limited to saredutant.

Beta-3 adrenoreceptor agonists include but are not limited to amibegron.

CRF1 antagonists include but are not limited to pexacerfont.

An anti-obesity agent may include a cannaboid receptor ligand, antagonist, or inverse agonist; a fatty acid amide hydrolase inhibitor; a peptide YY; a serotonin 5-HT2c antagonist; an adipocyte 11B-hydroxysteroid dehydrogenase type 1 antagonist; an amylase inhibitor; an anti-angiogenesis inhibitor; an agouti-related peptide analog, agonist, or antagonist; a carboxypeptidase inhibitor; a ciliary neurotrophic factor; a cholecystokinin (CCK) analog, agonist or inhibitor; a corticotrophin relating hormone modulator, agonist, or antagonist; a CKGGRAKDC peptide; a dehydroepiandrosterone analog; a fatty acid synthesis inhibitor; a fat-targeted peptide; a G-protein coupled receptor (GCPR) modulator; a gastrointestinal lipase inhibitor; a ghrelin modulator, agonist or antagonist; a human growth hormone (HGH) analog or fragment; a growth harmone secrectogue receptor (GHS—R) modulator, agonist or antagonist; a lipase inhibitor; a leptin analog, transport and/or receptor promoter; a melanocortin (MC) receptor agonist or antagonist; an M4 receptor agonist or antagonist; a melanin concentrating hormone (MCHR) agonist or antagonist; a melanocyte stimulating hormone analog; a neuropeptide Y modulator, agonist or antagonist; a thyroid hormone;
a thyroid receptor agonist; an orexin modulator, agonist or antagonist; a peptide YY or related analog or stimulator; a phytostanol analog; a pro-opiomelanocortin (POMC) stimulator; a somatostatin agonist; or a TNF-alpha antagonist.

An anti-diabetes agent may include a glucose-lowering (i.e., hypoglycemic) agent; an alpha-glucosidase inhibitor; an amylin analog; a biguanide; an incretin mimetic or analog; a glucagon-like peptide-1 (GLP-1) agonist or analog; a dipeptidyl peptidase (DPP) inhibitor; a DPP-IV inhibitor; a glucose-dependent insulinotropic peptide (GIP) agonist or analog; a gastric inhibitory peptide analog; a form of insulin (ie, injectable or inhaled); a fructose 1,6 biphosphatase (FBPase) inhibitor; a meglitinide; a peroxysome proliferators activated receptor (PPAR) modulator, agonist or antagonist; a PPAR-gamma agonist or antagonist; a protein-tyrosine phosphatase (PTP) 1B modulator, agonist or antagonist; a sodium-dependent glucose transporter (SGLT) inhibitor; a sulfonylurea; or a thiazolidinedione (ie, a "glitazone").

The invention includes combination methods of treatment in which an amphetamine prodrug, such as lisdexamfetamine dimesylate, a methylphenidate prodrug, or a methylphenidate analog is provided together with a Norepinephrine/Dopamine Reuptake Inhibitor, a Serotonin Reuptake Inhibitor, a Selective Serotonin Norepinephrine Reuptake Inhibitor, a Norepinephrine Reuptake Inhibitor, or an Anticonvulsant. For example the invention includes combination methods in which the amphetamine prodrug (e.g. lisdexamfetamine dimesylate) or methylphenidate prodrug is provided in combination with one or more of bupropion HCl, venlafaxine, paroxetine, mirtazapine, duloxetine, citalopram, escitalopram, fluoxetine, sertraline, atomoxetine, topiramate, zonisamide, lamotrigine, gabapentin, tiagabine, or pregabalin.

When treating binge eating the following active agents are particularly useful in combination with a methylphenidate prodrug or amphetamine prodrug: orlistat, bupropion, memantine, naltrexone, acamprosate, topiramate, zonisamide, sibutramine. Sibutramine may not be suitable for all patients because of its tendency to elevate pulse and blood pressure. Zonisamide is effective for treatment of binge eating but is not always well tolerated.

When treating depression the following active agents are particularly useful in combination with a methylphenidate prodrug or amphetamine prodrug: excitalopram, sertraline, fluoxetine, citalopram, bupropion, venlafaxine, and duloxetine.

Articles of Manufacture

The invention includes articles of manufacture, which comprise an amphetamine prodrug, methylphenidate prodrug, or methylphenidate analog in a container and labeling stating that the amphetamine prodrug, methylphenidate prodrug, or methylphenidate analog is effective for treating certain central nervous system disorders; including treating binge eating disorders, obesity resulting from binge eating behavior, and depression. The labeling may also state that the amphetamine prodrug, methylphenidate prodrug, or methylphenidate analog is effective for treating certain co-morbidities in ADHD and ADD patients; for example the invention includes methods of treating generalized anxiety disorder, obsessional and ruminative thought disorders, and obsessive/compulsive behavior in ADHD and ADD patients. The amphetamine prodrug, methylphenidate prodrug, or methylphenidate analog present in this article of manufacture may be lisdexamfetamine dimesylate or some other amphetamine prodrug, methylphenidate prodrug, or methylphenidate analog. The article of manufacture may comprise the amphetamine prodrug, methylphenidate prodrug, or methylphenidate analog as the only active agent or may include one or more additional active agents. Additional active agents may be combined in a single dosage form with the amphetamine prodrug, methylphenidate prodrug, or methylphenidate analog or may be packaged as separate dosage forms.

The article of manufacture may comprise packaging material and a dosage form of an amphetamine prodrug, methylphenidate prodrug, or methylphenidate analog contained within the packaging material, wherein the packaging material comprises a label approved by a regulatory agency for the product. In certain embodiments the labeling is labeling approved by the United States FDA.

An example of an article of manufacture provided by the invention is a packaged pharmaceutical compositions comprising an amphetamine prodrug, methylphenidate prodrug, or methylphenidate analog in a container and printed labeling stating that the amphetamine prodrug, methylphenidate prodrug, or methylphenidate analog is useful for treating a binge eating disorder or associated symptoms, obesity resulting from binge eating behavior, or depression.

When an article of manufacture of this invention comprises lisdexamfetamine dimesylate, the labeling may advise administering 2.5 mg to 250 mg, 2.5 mg to 12.5 mg, 2.5 to 15 mg, 10 to 100 mg per day, 20 to 70 mg per day, or about 50 mg per day lisdexamfetamine dimesylate. The labeling may advise that lisdexamfetamine dimesylate is to be administered once daily, but there may be clinical value in some patients for up to two times per day.

Pharmaceutical Preparations

An amphetamine prodrug, methylphenidate prodrug, or methylphenidate analog alone or in combination with one or more other active agent(s) can be administered as the neat chemical, but is preferably administered as a pharmaceutical composition or formulation. Accordingly, the invention provides pharmaceutical formulations comprising an amphetamine prodrug, methylphenidate prodrug, or methylphenidate analog alone or in combination with one or more other active agents together with one or more pharmaceutically acceptable carriers. Pharmaceutical formulations comprising lisdexamfetamine dimesylate have been previously described in U.S. Pat. No. 7,105,486, which is hereby incorporated by reference at cols. 13 to 17 for its teachings regarding amphetamine prodrug formulations including lisdexamfetamine dimesylate formulations.

An amphetamine prodrug, methylphenidate prodrug, or methylphenidate analog alone or in combination with one or more other active agent(s) may be administered orally, topically, parenterally, by inhalation or spray, sublingually, transdermally, via buccal administration, or by other means, in dosage unit formulations containing conventional non-toxic pharmaceutically acceptable carriers, excipients, adjuvants, and vehicles. Oral dosages forms such as tablets, troches, lozenges, aqueous or oily suspensions, dispersible powders or granules, emulsions, hard or soft capsules, or syrups or elixirs are preferred. Oral administration is preferred for lisdexamfetamine dimesylate administration. In some embodiments solid oral dosage forms are preferred. Tablets, capsules, and inhalable (e.g. intranasal) preparations are preferred. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations.

Oral formulations contain between 0.1 and 99%, at least about 5% (weight %), 25% to about 50% or from 5% to 75% of an amphetamine prodrug, methylphenidate prodrug, or methylphenidate analog alone or in combination with one or more other active agent(s) and usually at least about 5% (weight %) of a compound of the present invention.

In addition to the amphetamine prodrug, methylphenidate prodrug, or methylphenidate analog alone or in combination with one or more other active agent(s), the compositions of the invention may contain a pharmaceutically acceptable carrier, one or more compatible solid or liquid filler diluents or encapsulating substances, which are suitable for administration to an animal. Carriers must be of sufficiently high purity and sufficiently low toxicity to render them suitable for administration to the animal being treated. The carrier can be inert or it can possess pharmaceutical benefits of its own. The amount of carrier employed in conjunction with the compound is sufficient to provide a practical quantity of material for administration per unit dose of the compound.

The pharmaceutical dosage forms may contain an amphetamine prodrug, methylphenidate prodrug, or methylphenidate analog as the only active agent or may be combined with one or more additional active agents in the same dosage form. Active agents suitable for combination with an amphetamine prodrug, methylphenidate prodrug or methylphenidate analog in a single dosage form have been listed above in the section titled "Combination Methods." Particularly useful combination dosage forms include lisdexamfetamine in combination with at least one of the following in a single dosage form: orlistat, memantine, naltrexone, acamprosate, topiramate, zonisamide, sibutramine, escitalopram, sertraline, fluoxetine, citalopram, bupropion, venlafaxine, and duloxetine.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability. Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

The invention includes amphetamine prodrug capsule formulations, particularly lisdexamfetamine dimesylate capsule formulations,
2.5 mg to 250 mg, 2.5 mg to 12.5 mg, 2.5 to 15 mg, 10 to 100 mg per day, 20 to 70 mg per day, or about 50 mg per day lisdexamfetamine dimesylate together with one or more of microcrystalline cellulose, croscarmellose sodium, and magnesium stearate in a gelatin capsule. The invention also includes methylphenidate tablets comprising 2.5 to 200 mg methylphenidate prodrug together with lactose, magnesium stearate, polyethylene glycol, starch, sucrose, talc, and gum tragacanth.

EXAMPLES

The following examples describe patients with binge eating disorder or associated symptoms, a history of major depressive episodes, obsessive compulsive behavior, generalized anxiety disorder, or attention deficit hyperactivity disorder whose symptoms were poorly managed with psychopharmacologic interventions. In the cases where binge eating and depression were present, binge eating behavior significantly lessened following treatment with the amphetamine prodrug, lisdexamfetamine dimesylate; in one of these cases, it was thought that binge eating symptoms were due to antidepressant medication and the addition of amphetamine prodrug lisdexamfetamine dimesylate decreased binging behavior. Additionally, patients treated with lisdexamfetamine dimesylate, either as a monotherapy or as an adjunct to existing therapies, experienced remission of their depressive symptoms. The examples demonstrate the effectiveness of an amphetamine prodrug as a monotherapy or in combination with one or more other therapeutic agents for treating a range of psychological symptoms, including binge eating and depression.

These case reports suggest the clinical efficacy of an amphetamine prodrug, methylphenidate prodrug, or methylphenidate analog in the treatment of binge eating disorder or associated symptoms (in two cases thought to worsen from antidepressant agents), obesity resulting from binge eating behavior, and depressive disorders, as either a monotherapy or as an adjunct to existing antidepressant pharmacotherapy. In addition these cases also demonstrate that an amphetamine prodrug, a methylphenidate prodrug, or methylphenidate analog may offer significant clinical value in treatment of anxiety spectrum symptoms, include generalized anxiety disorder and obsessive compulsive behavior.

Example 1

Treatment of a Patient with Major Depressive Disorders and Binge Eating Disorder Using the Amphetamine Prodrug Lisdexamfetamine Dimesylate Patient 1 is an adult, non-geriatric patient with a history of a major depressive disorder, attention deficit hyperactivity disorder, and binge eating disorder. Throughout Patient 1's entire adult life, there were reportedly periodic depressive episodes and symptoms. Patient 1 also indicated a history of binge eating disorder for approximately one year, characterized by eating unusually large amounts of junk food, often until feeling nauseated, and then feeling very guilty about the binging behavior. Such symptoms, though intermittently present for the past two decades, had escalated to an average of nearly every other day for about 12 months. During this time Patient 1 was being treated with PAXIL (paroxetine) and then ZOLOFT (sertraline) daily. Patient 1 participated in group therapy to address mood and eating symptoms. However, group therapy did not prove helpful for managing the binging behavior; the number of episodes as well as the number of days binging continued on average every other day. Following group therapy, Patient 1 began to experience a worsening depressed mood, poor concentration, and excessive feelings of guilt, fatigue, and feelings of hopelessness. Prior treatments for this patient's major depressive disorder included PROZAC (fluoxetine), LEXAPRO (escitalopram), EFFEXOR (venlafaxine HCl), and WELLBUTRIN (bupropion Hal). Lisdexamfetamine dimesylate was added to Patient 1's 100 mg ZOLOFT (sertraline) therapy as this patient met criteria of attention deficit hyperactivity disorder, with both inattention and hyperactivity symptoms present since childhood, though this diagnosis was not previously made for Patient 1. The dose of lisdexamfetamine dimesylate was titrated from 30 mg, to 50 mg, to 70 mg, in three successive weeks, respectively. Patient 1 reported significant improvement in the prior symptoms of inattention, forgetfulness, procrastination and physical restlessness, among others, by the time Patient 1 was taking 70 mg of lisdexamfetamine dimesylate daily. Patient 1 was maintained on that dose for an ensuing 8 weeks, along with 100 mg ZOLOFT (sertraline), and reported having no more than 3 or 4 binging episodes in total and no more than 3 binging days for the 8 weeks that Patient 1 was maintained at 70 mg lisdexamfetamine dimesylate daily.

Patient 1 experienced a reduction from approximately 12 or more binge eating days per month, present for approximately one year, to no more than 3 per month while taking the amphetamine prodrug lisdexamfetamine dimesylate, an approximately 75% reduction of binging eating days per month. Patient 1 also noted full remission of depressive symptoms for the 8 weeks of maintenance on 70 mg lisdexamfetamine dimesylate in addition to 100 mg ZOLOFT (sertraline) noting significant improvement in depressed mood, concentration, feelings of guilt, fatigue and no longer experienced any sense of hopelessness.

Example 2

Treatment of a Patient with Binge Eating Disorder and Major Depressive Disorders Using Lisdexamfetamine Dimesylate Patient 2 is a non-geriatric adult with a history of attention-deficit hyperactivity disorder, polysubstance dependence, major depressive disorder, generalized anxiety disorder, and binge eating disorder. The patient has been treated in the past with multiple medication trials, either alone or in combination, including: WELLBUTRIN (bupropion HCl), EFFEXOR (venlafaxine HCl), CELEXA (citalopram), LAMICTAL (lamotrigine), RISPERDAL (risperidone), NEURONTIN (gabapentin), KLONOPIN (clonazepam), STRATTERA (atomoxetine) CONCERTA (methylphenidate), RITALIN SR (methylphenidate), ADDERAL XR (dextroamphetamine+amphetamine), and PROVIGIL (modafinil). The patient also was previously treated with intensive psychotherapy and received various forms of substance abuse counseling in the past. Lisdexamfetamine dimesylate was initiated for treatment of the patient's ADHD to address 'wear off' effects from ADDERALL XR in the later afternoons and early evenings. While the patient experienced an underlying mild depressive disorder, such "wear off" effects correlated with worsening of an already mildly depressed mood, further lowered overall energy level, even poorer concentration and unsettled sleep. The patient also indicated hinging behavior in the evenings, typically characterized by rapidly devouring large amounts of "sweet" foods, while alone, and until feeling bloated. While the patient struggled with binging behavior for the past two decades, the binge eating symptoms intensified in the 6 months prior to starting lisdexamfetamine dimesylate treatment, occurring at least two days per week, and causing an approximately 30 pound weight gain. Lisdexamfetamine dimesylate treatment was initiated, primarily for treatment of Patient 2's attention deficit hyperactivity disorder to provide greater coverage into the evening, with a dosing schedule of 30 mg on day 1, 50 mg on day 2, and 70 mg on day 3; the patient had been taking Adderall XR 30 mg per day, which was discontinued on day 1 of starting lisdexamfetamine dimesylate. The patient was maintained on lisdexamfetamine dimesylate for about 10 weeks.

Patient 2 noted an overall improvement in depressive symptoms, including depressed mood, general interest level in activities especially in the evenings, sleep quality, and physical fatigue. Patient 2 also noted a marked reduction in binging episodes, both in terms of the total number and total days of binges; such binging episodes occurred only once in the first 2 weeks of treatment and stopped entirely in the subsequent 8 weeks of treatment with lisdexamfetamine dimesylate. The patient, considered obese prior to starting lisdexamfetamine dimesylate, lost approximately 7% of total body weight while taking the amphetamine prodrug. Interestingly, triglyceride levels present prior to taking lisdexamfetamine dimesylate were 271 mg/dL and reduced to 160 mg/dL by the end of 5 weeks of treatment with lisdexamfetamine dimesylate.

This case report exemplifies the utility of an amphetamine prodrug as a monotherapy for depression treatment, as demonstrated in this patient with an underlying depressive disorder, untreated with antidepressant medication at the time of initiating lisdexamfetamine dimesylate, who showed significant improvement across all the patient's depressive symptoms. The effectiveness of lisdexamfetamine dimesylate monotherapy in treating the patient's treatment resistant depression is particularly remarkable in view of Patient 2's number of failed treatments of recurrent major depressive disorder. Prior treatments failed due to poor treatment response and medication side effect intolerability. It should be noted that Patient 2's ADHD symptoms were not at issue at the time lisdexamfetamine dimesylate monotherapy was begun. The patient's ADHD symptoms were adequately addressed with ADDERALL XR treatment. Lisdexamfetamine dimesylate monotherapy was started to address the adverse effects Patient 2 had experienced from ADDERALL XR treatment. Lisdexamfetamine dimesylate proved as effective as ADDERALL XR in addressing the patient's ADHD symptoms, demonstrated sustained and full day antidepressant efficacy, and functioned as an antidepressant in addition to alleviating ADHD symptoms.

Example 3

Treatment of a Patient with ADHD, Generalized Anxiety Disorder, and Obsessive-Compulsive Behavior Using Lisdexamfetamine Dimesylate The patient is a non-geriatric adult diagnosed with a history of ADHD, inattentive type, and comorbid Generalized Anxiety Disorder, though had no prior treatment. Presenting ADHD symptoms included difficulty sustaining attention and attending to details, difficulty organizing tasks with tendencies toward avoidance, distractibility, and problems finishing tasks that have been initiated. Symptoms of Generalized Anxiety Disorder included frequent and intense ruminative worrying, feeling overly fatigued, muscle tension and intermittent problems with sleep. History suggests that a perseverative pattern of thinking and compulsive worrying may have evolved from deficits in attention and information processing. The patient was started on VYVANSE 30 mg in the morning, along with TRAZODONE 50 mg at bedtime. VYVANSE was maintained at 30 mg once daily in the morning for one week, followed by one week at 50 mg per day, and then 70 mg per day, taken in the morning. The patient experienced a positive effect across all ADHD and Generalized Anxiety Disorder symptoms within the first week, with more dramatic improvement as the dose of VYVANSE was increased. The patient maintained treatment on VYVANSE at 70 mg per day for 10 weeks; TRAZODONE 50 mg at bedtime was discontinued after 4 weeks as sleep patterns had sufficiently normalized. While maintained on VYVANSE at 70 mg per day, the patient noted significantly enhanced ability to sustain attention and attend to details, organize and finish projects, and process information as compared to previous baseline function, with clear and evident improvements in work function. The patient found, surprisingly, a highly significant improvement on compulsive ruminating and worrying. The patient previously felt little or no control around such worrying, ruminative behavior and speculated that it caused significant mental and even physical fatigue. After 10 weeks of treatment with VYVANSE at 70 mg per day, the patient reported being only mildly affected by inattention symptoms and preoccupied primarily with 'realistic kinds of worries' that were generally well-managed.

This case demonstrates the use of an amphetamine prodrug lisdexamfetamine dimesylate as monotherapy for comorbid ADHD and anxiety spectrum symptoms, most notably generalized anxiety (in this case Generalized Anxiety Disorder) that took on a perseverative and 'compulsive worrying' quality along with physical symptoms of fatigue and muscle tension. Stimulant medications have traditionally been associated with causing or worsening anxiety symptoms (for instance, being 'anxiogenic'). It is thus surprising that an amphetamine prodrug proved useful for treating the Generalized Anxiety Disorder symptoms for the duration of the day, with no problematic 'wear off'.

Example 4

Treatment of Patient with Comorbid Depressive Disorders and Binge Eating Behavior with Lisdexamfetamine Dimesylate The patient is a non-geriatric adult with a history of intermittent major depressive disorder, dysthymic disorder, and binge eating behavior. The patient also endorsed symptoms of ADHD, inattentive type, primarily around problems with organizing tasks, procrastination of work activities, and problems completing projects, though such 'inattention' symptoms were considered as clinically less detrimental than feeling chronically depressed, lacking motivation or interest in work or social activities, feeling fatigued and sometimes guilty, and having gained weight over several years due to 'emotional eating' behavior. The patient had received therapy in the past to address depressive episodes and associated life stressors, with modest benefit. The patient also described a history of 'emotional eating' that could occur at any time of day though more often in the late afternoons or early evenings. Such 'emotional eating' was often triggered by stressful situations or events, accompanied by an urge to eat, and would typically lead to excess consumption of carbohydrate-based foods. In recent years, the patient reported having gained over 10% body weight and noted a general trend toward increasing emotional eating and binging behavior. More severe binges occurred at least several times per month over a stretch of several years, though were much less common than 'emotional eating' that was milder in nature and occurred nearly daily. Medication treatment was initiated with VYVANSE at 30 mg per day for two weeks and the dose was increased to 50 mg per day, without any adverse effects. The patient was maintained on VYVANSE for 10 weeks at 50 mg per day. The patient reported a rather abrupt and sustained cessation of emotional eating behavior in the afternoon while taking 50 mg VYVANSE daily. Symptoms of emotional eating were improved in the evenings as well, with less than one per week on average as compared to most evenings previously. There were no reported major binges reported at any point while taking VYVANSE and the patient lost approximately 6-7 pounds over 2½ months of treatment. The patient also noted significant amelioration of depressive symptoms, of feeling chronically low, and felt sufficiently motivated and invested in work and social activities in a way that was not present for some time. The organization and execution of work-related tasks improved during the course of treatment as well.

The case report demonstrates successful treatment of a comorbid depressive disorder (both major depressive disorder and dysthymic disorder) and binge-eating behavior with the amphetamine prodrug lisdexamfetamine dimesylate. The patient also began a trend of weight loss on account of decreased emotional eating and binging. The patient's ADHD was also clinically relevant, which is the primary reason VYVANSE was chosen as the initial medication treatment, though it was not the reason for which evaluation and treatment was sought and of secondary importance with regard to symptoms causing the patient difficulty and concern. Clinical improvement on depressive symptoms was present, most notably improved interest in daily activities and overall mood. Binge-eating behavior, largely taking the form of 'self-soothing' eating activity with potentially serious risks in this patient insofar as it was causing steady increased weight gain to the point of obesity), responded remarkably well to treatment with VYVANSE. The patient's symptoms of ADHD, inattentive type, also demonstrated improvement and enhanced an overall sense of improved well being, effectiveness, and confidence.

Example 5

Treatment of Binge Eating Disorder, Medication-Induced Cognitive Problems, and Fatigue with Lisdexamfetamine Dimesylate The patient is a non-geriatric adult with a history of recurrent major depressive disorder with comorbid anxiety symptoms and severe binge eating disorder. The patient previously has been treated with therapy and has had multiple prior medication trials, either discontinued due to lack of efficacy or side effects, including ZOLOFT (sertraline), CELEXA (citalopram), PROZAC (fluoxetine), LEXAPRO (escitalopram), WELLBUTRIN SR (bupropion HCl), NORTRIPTYLINE, ATIVAN (lorazepam), ABILIFY (aripiprazole), RISPERDAL (risperidone), SEROQUEL (quetiapine), LYRICA (pregabalin), and RITALIN (methylphenidate). Selective serotonin reuptake inhibitors exacerbated binge eating symptoms and caused problematic weight gain. For treatment of depression with comorbid anxiety, binge-eating, and weight-gain related to binge eating symptoms, the patient was maintained on a medication regimen that included TOPAMAX (topiramate) 175 mg in the morning and 200 mg at night, LAMICTAL (lamotrigine) 200 mg in the morning, CYTOMEL (liothyronine) 25 mcg per day, KLONOPIN (clonazepam) 0.25 mg at bed time, and NEURONTIN (gabapentin) 600 mg at bedtime. However, symptoms of depressed mood, hopelessness, amotivation, problems with concentration (possibly worsened with the use of TOPAMAX though prior attempts to decrease the dose exacerbated binge-eating symptoms), significant fatigue, and tendency toward emotional eating and binging significantly increased from baseline. Given prior poor response to a number of different classes of medication trials, off-label use of VYVANSE was initiated at 30 mg each morning to target a constellation of symptoms, including symptoms of major depression, binge-eating disorder, fatigue, and concentration problems. VYVANSE was maintained at 30 mg each morning for weeks before being discontinued due to adverse effects. These side effects were excessive appetite suppression and visual blurring. However, during the time of treatment, the patient indicated a notably reduced urge to binge, fewer absolute binges per week, fewer binge-eating days per week, and improvement in both fatigue and concentration throughout the day. However, there appeared to be no benefit on the patient's depressed mood, amotivation, and feelings of hopelessness.

This case exemplifies the clinical benefit of lisdexamfetamine dimesylate on binge-eating symptoms and potentially on weight-gain related to binging (body weight was not obtained), though longer-term treatment was cut short by adverse effects at the 30 mg dosage form. Given the number of failed prior trials, off-label use of VYVANSE was clinically indicated, especially given the severity of binge eating behavior. Though TOPAMAX helped reduce binge eating behavior, it was clinically insufficient to fully address binge eating behavior, as it was poorly tolerated at higher doses due to cognitive side effects, and may have had a contributory role in cognitive slowing and fatigue at the maintenance dose.

Example 6

Treatment of a Patient with Comorbid Generalized Anxiety Disorder, Major Depression, and ADHD with Lisdexamfetamine Dimesylate Patient 6 is a non-geriatric adult with a history of Generalized Anxiety Disorder and Major Depressive Disorder. The patient was maintained on PAXIL (paroxetine) 30 mg per day following a significant comorbid major depressive episode associated with anxiety symptoms, and a history consistent with Generalized Anxiety Disorder. Treatment with PAXIL had rapidly stabilized both depressive and anxiety symptoms and for approximately 2 years the patient was maintained at 30 mg per day with no change in dose. Over this time, the patient had gained approximately 10% of their body weight. It was periodically addressed that the patient may have experienced previous academic difficulties due to ADHD, inattentive type, though during the course of treatment with PAXIL, the patient was generally able to adapt to work pressures and developed compensatory strategies to deal with organizational difficulties, auditory inattention and forgetfulness, and feeling poorly engaged. However, after beginning a new job with more challenging responsibilities, the patient was unable to compensate for such deficits and a pattern of obsessive ruminations emerged, often involving work. In addition to perseverative and obsessive thinking, the patient experienced heightened anxiety and mild depressive symptoms, including fatigue, low mood, and amotivation, especially while at work. After discussing medication options and side effect concerns, VYVANSE was initiated to address underlying ADHD symptoms, which were felt to drive the patient's perseverative thinking, anxious ruminations, and low mood. VYVANSE was initiated at 30 mg per day for one week, and then titrated to 50 mg per day, without adverse effect. PAXIL was maintained at 30 mg per day. Over the course of the ensuing 9 weeks, the patient reported improvement across ADHD, Generalized Anxiety Disorder, and Major Depressive Disorder symptoms. Work function began to feel 'easier', with better ability to attend to tasks and more efficient performance, improved attention to detail, and feeling internally less restless. The patient reported a substantial reduction in worrying, an approximate 4-5% weight loss over 2 months of treatment, and improved mood, motivation and energy.

The case report exemplifies the use of the amphetamine prodrug lisdexamfetamine dimesylate to address multiple clinical issues, the most unexpected one being the alleviation in generalized anxiety symptoms, perseverative thinking, and obsessive ruminations. The patient's initial presenting symptoms in past treatment have been within the class of Anxiety Disorders, mainly of Generalized Anxiety Disorder but also possibly Obsessive-Compulsive Disorder, as well as within the class of Depressive Disorders, mainly Major Depressive Disorder. While the patient may have exhibited ADHD symptoms in the past, they were considered clinically of a secondary nature, such that pharmacologic treatment had been initiated with the selective serotonin reuptake inhibitor (SSRI) PAXIL (paroxetine) to target both depressive and anxiety spectrum symptoms. The use of the amphetamine prodrug VYVANSE was able to accomplish a number of clinically very important objectives, with full-day duration effects, including augmentation of the mood-enhancing effect of the antidepressant PAXIL, alleviation of anxiety spectrum symptoms (including worrying and obsessive/compulsive mental behavior), and reduction of ADHD symptoms.

What is claimed is:

1. A method of treating Binge Eating Disorder, comprising diagnosing a patient as having Binge Eating Disorder, wherein the patient exhibits Binge Eating Disorder as defined in the DSM-IV-TR and administering a therapeutically effective amount of lisdexamfetamine dimesylate to the patient, wherein the lisdexamfetamine dimesylate is the only active agent administered or is administered together with one or more additional active agents.

2. The method of claim 1, wherein 15 to 70 mg lisdexamfetamine dimesylate is administered daily.

3. The method of claim 1 wherein the lisdexamfetamine dimesylate is administered together with one or more other active agent(s).

4. The method of claim 3, wherein the one or more other active agent(s) is an appetite suppressant, a weight loss drug, an anti-obesity agent, an anti-diabetes agent, a selective serotonin reuptake inhibitor, a serotonin 5HT receptor partial agonist or antagonist, a norepinephrine dopamine reuptake inhibitor, a serotonin norepinephrine dopamine reuptake inhibitor, a serotonin norepinephrine reuptake inhibitor, a nicotinic acetylcholine receptor agonist or antagonist, an anti-convulsant, a glutamate modulator, an opioid antagonist, or a combination of the foregoing.

5. The method of claim 4, wherein the other active agent is orlistat, sibutramine, phentermine, rimonabant, acamprosate, adiponectin, benzphetamine, butabinide, cetilistat, cholecystokinin, diethylpropion, d-cycloserine, lorcaserin, naltrexone, 6-beta-naltrexol, buprenorphine, octreotide, oleoyl-estrone, oxytocin, phenylpropanolamine, phendimetrazine, phentermine, sodium oxybate, tesofensine, thyroxine, acarbose, acipimox, chlorpropamide, diazoxide, exenatide, gliclazide, glimepiride, glipizide, glucagon, glyburide, liraglutide, metformin, miglitol, nateglinide, pioglitazone, pramlintide, repaglinide, rosiglitazone, saxagliptin, sitagliptin, tolazamide, vildagliptin, dapagliflozin, sergliflozin, clovoxamine, femoxetine, flesinoxan, citalopram, escitalopram, fluoxetine, fluvoxamine, sertraline, duloxetine, desvenlafaxine, venlafaxine, atomoxetine, reboxetine, thionisoxetine, bupropion, mianserin, buspirone, amantadine, bromocriptine, cabergoline, lisuride, pergolide, pramipexole, ropinirole, vanoxerine, amisulpride, lamotrigine, levetiracetam, topiramate, zonisamide, modafinil, armodafinil, varenicline, galantanaine, memantine, or pharmaceutically active salts thereof, or a combination of the foregoing.

6. The method of claim 5, wherein the other active agent is orlistat, naltrexone, or zonisamide, or a pharmaceutically acceptable salt or hydrate of any of the foregoing.

7. The method of claim 6, wherein the other active agent is naltrexone.

8. A method of treating Binge Eating Disorder, comprising diagnosing a patient as having Binge Eating Disorder, wherein the patient exhibits Binge Eating Disorder as defined in the DSM-IV-TR and administering a therapeutically effective amount of lisdexamfetamine dimesylate to the patient wherein the lisdexamfetamine dimesylate is the only active agent administered.

9. The method of claim 8 wherein from 2.5 to 200 mg of lisdexamfetamine dimesylate is administered daily.

10. The method of claim 8, wherein 15 to 100 mg lisdexamfetamine dimesylate is administered once per day.

11. The method of claim 8, wherein the effective amount is an amount effective to decrease the number of binge eating episodes per month or decrease the number of days in a month in which the patient experiences a binge eating episode.

12. The method of claim 8, wherein 15 to 70 mg lisdexamfetamine dimesylate is administered daily.

13. A method of treating Binge Eating Disorder as defined in the DSM-IV-TR, comprising administering a therapeutically effective amount of lisdexamfetamine dimesylate to a patient in need thereof, wherein the lisdexamfetamine dimesylate is the only active agent administered or is administered together with one or more additional active agents.

* * * * *

(12) INTER PARTES REVIEW CERTIFICATE (114th)
United States Patent
Sanfilippo

(10) Number: US 8,318,813 K1
(45) Certificate Issued: Jan. 12, 2016

(54) METHOD OF TREATING BINGE EATING DISORDER

(75) Inventor: Louis Sanfilippo

(73) Assignee: LUCERNE BIOSCIENCES LLC

Trial Number:
  IPR2014-00739 filed May 9, 2014

Petitioner: Shire Development LLC

Patent Owner: Lucerne Biosciences, LLC

Inter Partes Review Certificate for:
  Patent No.: 8,318,813
  Issued: Nov. 27, 2012
  Appl. No.: 12/666,460
  Filed: Oct. 6, 2010

The results of IPR2014-00739 are reflected in this inter partes review certificate under 35 U.S.C. 318(b).

INTER PARTES REVIEW CERTIFICATE
U.S. Patent 8,318,813 K1
Trial No. IPR2014-00739
Certificate Issued Jan. 12, 2016

AS A RESULT OF THE INTER PARTES REVIEW PROCEEDING, IT HAS BEEN DETERMINED THAT:

Claims 1-13 are cancelled.

\* \* \* \* \*